United States Patent [19]
Shealy et al.

[11] Patent Number: 5,891,853
[45] Date of Patent: Apr. 6, 1999

[54] COMPOSITIONS AND METHODS FOR ENHANCEMENT OF DEHYDROEPIANDROSTERONE

[75] Inventors: C. Norman Shealy, Fair Grove, Mich. 65648; Cay Randall-May, Phoenix, Ariz.

[73] Assignee: C. Norman Shealy, Fair Grove, Mich.

[21] Appl. No.: 35,548

[22] Filed: Mar. 5, 1998

Related U.S. Application Data

[63] Continuation of Ser. No. 766,427, Dec. 12, 1996, Pat. No. 5,753,696.
[51] Int. Cl.$^6$ .......................... A61K 31/70; A61K 31/34; A61K 31/095
[52] U.S. Cl. .................. 514/23; 514/474; 514/706
[58] Field of Search ............................... 514/474, 23, 706

[56] References Cited

U.S. PATENT DOCUMENTS

| | | |
|---|---|---|
| 4,518,595 | 5/1985 | Coleman et al. . |
| 4,559,329 | 12/1985 | Herschler . |
| 4,774,093 | 9/1988 | Provonchee et al. . |
| 4,835,147 | 5/1989 | Roberts . |
| 5,071,878 | 12/1991 | Herschler . |
| 5,077,284 | 12/1991 | Loria et al. . |
| 5,110,810 | 5/1992 | Eich et al. . |
| 5,162,198 | 11/1992 | Eich et al . |
| 5,609,617 | 3/1997 | Shealy et al. . |

OTHER PUBLICATIONS

S. Kent, "DHEA: 'Miracle' drug?", Geriatrics for the Primary Care Physician, vol. 37, No. 9, 1982, pp. 157–159.

N. Orentreich, et al., "Age Changes Sex Differences in Serum Dehydroepiandrosterone Sulfate Concentrations throughout Adulthood", The Journal of Clinical Endocrinology & Metabolism, vol. 59, No. 3, 1984, pp. 551–555.

Sulfate Concentrations throughout Adulthood , *The Journal of Clinical Endocrinology & Metabolism*, vol. 59, no. 3, 1984, pp. 551–555.

E. Barret–Connor, et al., "A Prospective Study of Dehydroepiandrosterone Sulfate, Mortality, and Cardiovascular Disease," The New England Journal of Medicine, vol. 315, No. 24, 1986, pp. 1519–1524.

G.B. Gordon, et al., "Reduction of Atherosclerosis by Administration of Dehydroepiandrosterone," The Journal of Clinical Investigation, vol. 82, No. 2, 1988, pp. 712–720.

W. Regelson, et al., "Hormonal Intervention: 'Buffer Hormones' or 'State Dependency'," vol. 518, 1988, pp. 260–273.

Y. Arad, et al., "Dehydroepiandrosterone Feeding Prevents Aortic Fatty Streak Formation and Cholersterol Accumulation in Cholesterol–fed Rabbit," Arteriosclerosis, vol. 9, No. 2, 1989, pp. 159–166.

C. Norman Shealy, *DHEA: the Youth and Health Hormone*, (A Keats Good Health Guide, 1996).

C. Norman Shealy, "A Review of Dehydroepiandrosterone (DHEA)," Intergrative Physiological and Behavioral Science, vol. 30, No. 4, 1995, pp. 308–313.

C. Norman Shealy, "DHEA Deficiency in Patients with Chronic Pain and Depression," J. Neurol. Orthop. Med. Surg., vol. 17, 1996, p. 6.

*Primary Examiner*—Raymond Henley, III
*Attorney, Agent, or Firm*—Foley & Lardner

[57] ABSTRACT

Compositions and methods for using the same to restore dehydroepiandrosterone (DHEA) levels in humans are described. Compositions comprising methyl sulfonyl methane and vitamin C, and additionally beta-1,3-glucan, are administered to humans to enhance DHEA levels. The compositions can be taken in various forms, such as a dried powdered mix with liquid, or as a pill, tablet, or capsule.

11 Claims, No Drawings

COMPOSITIONS AND METHODS FOR ENHANCEMENT OF DEHYDROEPIANDROSTERONE

This application is a continuation of application Ser. No. 08/766,427, filed Dec. 12, 1996, now U.S. Pat No. 5,753,696.

FIELD OF THE INVENTION

This invention pertains to compositions and methods for using the same to enhance serum levels of dehydroepiandrosterone ("DHEA") in human beings without administration of exogenous dehydroepiandrosterone or salts thereof.

BACKGROUND OF THE INVENTION

Dehydroepiandrosterone, also known as prasterone, 3-hydroxyandrost-5-en-17-one, dehydroisoandrosterone, trans-dehydroandrosterone, or $\Delta^5$-androsten-3-$\beta$ol-17-one (referred to hereinafter as "DHEA"), is a 17-ketosteroid, which is quantitatively one of the major adrenocortical steroid hormones present in the metabolism of humans and other mammals. S. Budavari, ed., Merck Index, Eleventh Edition (1989). This endogenous androgenic steroid has been shown to have a myriad of biological activities. An assortment of prior art has recognized the plethora of beneficial effects of DHEA, its sulfate ester (DHEA-S) and salts thereof. DHEA is readily interconvertible in vivo with DHEA-S through the action of intracellular sulfatases.

In U.S. Pat. No. 4,920,115 to Nestler et al., oral dosages of DHEA given to healthy male individuals were shown to reduce body fat mass, increase muscle mass, lower LDL cholesterol levels without affecting HDL cholesterol levels, and not affect tissue sensitivity to insulin in human patients. Nestler et al. described the use of pharmaceutical preparations of DHEA as a preventative means to avoid development of atherosclerosis.

U.S. Pat. Nos. 5,110,810 and 5,162,198 issued to Eich et al., disclose methods for treating human beings with pharmacological quantities of DHEA, resulting in increased serum DHEA and DHEA-S in their blood, which lowers rates of platelet aggregation. By reducing the rate of platelet aggregation, the incidence of morbidity and mortality from vascular events such as myocardial infarction and stroke, as well as the occurrence of restenosis following vascular interventions, can be significantly reduced.

U.S. Pat. No. 4,835,147 to Roberts demonstrated that administration of DHEA or its therapeutically acceptable salts to individuals ameliorated symptoms of prostatic hypertrophy, certain symptoms of menopause, particularly those related to nervous system dysfunction, and of psychosexual dysfunction, symptoms such as inhibited sexual desire, inhibited sexual excitement and inhibited orgasm.

Other widely varying medical uses for DHEA have been reported. U.S. Pat. No. 4,628,052, issued to Peat, reports using either an oral or topical preparation of DHEA to treat rheumatoid arthritis, osteo-arthritis and arthritis associated with psoriasis and with lupus and other auto-immune diseases, and also for treating non-specific joint pain associated with stress or incidental to other ailments.

DHEA compounds have also been established to have a beneficial effect as an anti-diabetic agent. See U.S. Pat. No. 4,518,595 to Coleman et al.

In the medical literature, many favorable reports of medical benefits to individuals due to increased levels of DHEA and its sulfate ester, DHEA-S, have been reported as well. *Geriatrics* 37:157 (1982) stated that DHEA was a "miracle" drug, which may prevent obesity, aging, diabetes mellitus and heart disease. Barrett-Conner et al. produced studies which revealed an inverse relationship between cardiovascular death and serum DHEA-S levels in adult men. *N. Engl. J. Med.* 315:1519 (1986). Arad et al. in *Arteriosclerosis* 9:159 (1989) and Gordon et al. in *J. Clin. Invest* 82:712 (1988) both describe the reduction of atherosclerosis plaque formation by DHEA.

One of the most important uses of DHEA has been to improve the immune response in human beings. U.S. Pat. No. 5,077,284, issued to Loria et al., describes the administration of DHEA, either orally or by subcutaneous injection, to provide very high levels of protection against viral, bacterial, fungal or parasitic infections in immunocompromised animals and humans. The experimental animal data, described by Loria et al., demonstrated that in infection (100,000 plaque forming units/animal) of a human coxsackievirus B4 strain, which causes mortality in about 90% of infected animals, mortality was reduced to 37% when animals were treated with DHEA. Moreover, Loria et al. demonstrated that administration of DHEA induced an 80% elevation in the number of antibody forming cells within the animal. In virus infected and DHEA treated animals, there was also an elevation in the number of monocyte cells, the particular white blood cells associated with a resistance to coxsackievirus infection. This elevation was not observed in uninfected animals that were treated with DHEA. This observation demonstrates that DHEA can be used to up-regulate the host immune response to virus infection, by increasing the number of antibody forming cells, elevating the number of white blood cells associated with resistance to virus infection and markedly reducing virus induced mortality.

Although DHEA is the most abundantly produced adrenal steroid and serum concentrations of its sulfate ester, DHEA sulfate (DHEA-S), are approximately 20 fold higher than those of any other circulating steroid hormone, levels of this hormone begin to decline within individuals during the second decade of life, reaching 5% of the original level in the elderly.

Peak serum DHEA and DHEA-S levels occur when a patient is approximately 25 years old and decline over the ensuing decades. Ohrentreich et al. found that mean DHEA-S levels and ranges for adult men were as follows: Ages 25–29 (3320 ng/ml); ages 45–49 (1910 ng/ml); ages 65–69 (830 ng/ml). See *J. Clin. Endocrinol. Metab.*, 59:551 (1984). Similar age related decline in serum DHEA-S levels were found to occur in women. Correspondingly, the incidence of cardiovascular disease in human beings increases with age, thus suggesting an epidemiological relationship between serum DHEA and DHEA-S levels in cardiovascular disease. In Barrett-Conner et al., supra, the baseline DHEA-S levels of 242 middle aged men (ages ranging between 50 and 79 years) was compared to the subsequent 12 year mortality rate of the men from any cause, from cardiovascular disease, and from ischemic heart disease. DHEA-S levels were significantly lower in men with a history of heart disease compared to those without. In men with no history of heart disease, the age-adjusted relative risk associated with DHEA-S levels below 140 $\mu$g/dl was 1.5 (p NS) for death from any cause, 3.3 (p<0.05) for deaths from cardiovascular disease, and 3.2 (p<0.05) for deaths from ischemic heart disease. An increase in DHEA-S level of 100 $\mu$g/l had a 48% reduction in mortality (adjusted for other risk factors) from cardiovascular disease (p<0.05).

Further Eich et al. supra, demonstrated that treating human beings with pharmacological quantities of DHEA resulted in increased serum levels of DHEA and DHEA-S. Eich et al. performed in vivo experiments using a test group of 10 male human being subjects. In these experiments, DHEA was administered in a double-blind placebo controlled trial in an amount of 300 mg of DHEA per day in the form of 100 mg capsules taken orally 3 times a day. The study found that the initial baseline serum DHEA prior to conducting the experiment was 5.83+/−3.9 ng/ml, and the mean serum DHEA during the second week of investigation for the placebo group was 5.58+/−4.1 ng/ml. The mean serum DHEA for the treated group during the second week investigation was 28.7+/−13.9 ng/ml. In addition, the baseline serum DHEA-S was 316.2 $\mu$g/dl and during the second week, the mean serum DHEA-S level was 260.5+/−56.7 $\mu$g/dl in the placebo group, and 1451.9+/−56.7 $\mu$g/dl in the DHEA group. Elevation of serum DHEA-S levels when a patient is receiving only supplemental DHEA suggested that DHEA-S serves as a storage pool for DHEA, which is the active form of the hormone. The rate of platelet aggregation for the human subjects participating in this study was examined prior to treatment with supplemental DHEA and was again tested on three different occasions during the second week of an investigation. Four of the five test subjects who received the DHEA supplement demonstrated a slower rate of aggregation and a requirement for higher concentration of arachidonic acid to initiate aggregation. Thus, the elevated serum DHEA level slowed platelet aggregation which can significantly reduce the incidence of morbidity and mortality from vascular events such as myocardial infarction and stroke.

SUMMARY OF THE INVENTION

The present invention provides compositions and methods for using the same for enhancing or restoring DHEA in a living human being. Because DHEA is a naturally occurring steroid, it has been found that endogenous production of the hormone may be stimulated by these compositions and methods, without the use of pharmaceutical preparations containing DHEA, its sulfate ester DHEA-S, or salts thereof.

One object of the invention is to provide compositions for elevating serum DHEA levels in an individual, which compositions comprise effective amounts of methyl sulfonyl methane and vitamin C; the compositions may comprise additionally effective amounts of beta-1,3-glucan. Another object is to provide methods for elevating serum DHEA levels in an individual by using said compositions.

It has been found that the greatest increase in serum DHEA levels occurred in patients treated with methyl sulfonyl methane, vitamin C and beta-1,3-glucan consumed on a daily basis; this regimen was effective in elevating DHEA levels in patient's serum by 50% to 150%.

DETAILED DESCRIPTION OF THE INVENTION

It has been found that DHEA levels may be raised in human beings without the application of exogenous supplements of DHEA, DHEA-S, or their corresponding salts. Treatments consisting of administering a composition comprising effective amounts of methyl sulfonyl methane and vitamin C, and additionally of beta-1,3-glucan, on a daily basis for a period of one week or longer, have been surprisingly and unexpectedly found to increase production of DHEA.

Stimulating natural biosynthesis of DHEA within the body is advantageous over the heretofore known methods of raising serum DHEA levels which consisted of administering DHEA, DHEA-S, or salts thereof, either parenterally, intravenously, subcutaneously, or transdermally. Clinical studies of treatments involving administration of DHEA, its esters, or salts thereof, have shown undesirable side effects associated with administration of the hormone. These side effects include mild androgenic effects and hirsutism. See W. Regelson et al., *New York Academy of Sciences*, 518:260 (1988). Side effects from the ingestion of DHEA, and other undesirable consequences involving the method of DHEA administration, can be avoided with the method of the present invention. No side effects have been detected from utilization of the present invention to raise DHEA levels in patient's blood.

The effective compositions herein described have been found to raise serum DHEA levels in human beings. These compositions comprise an effective amount of methyl sulfonyl methane, and an effective amount of vitamin C, which together exhibit activity increasing serum DHEA levels. The compositions may comprise in addition an effective amount of beta-1,3-glucan, which composition also exhibits activity increasing serum DHEA levels. In one embodiment of the present invention, the effective dose of methyl sulfonyl methane is preferably in the range of about 750 to 1500 mg/day and all subranges therein, and the effective dose of vitamin C is preferably in the range of about 1000 to 2000 mg/day and all subranges therein. Most preferably, the effective dose of methyl sulfonyl methane is about 1,500 mg/day, and the effective dose of vitamin C is about 2,000 mg/day. In another embodiment of the invention, which comprises in addition beta-1,3-glucan, the effective dose of beta-1,3-glucan is preferably in the range of about 2 to 6 mg/day, and all subranges therein. Most preferably, the effective dose of beta-1,3-glycan is about 2 to 3 mg/day.

The compositions can be administered orally in various formulations, such as in a dried powdered mix with liquid, or a pill, a tablet, or a capsule. The compositions can be taken daily, either one or more times a day, or as otherwise prescribed.

In accordance with the invention, it has been surprisingly and unexpectedly discovered that administration of the disclosed compositions can raise DHEA levels in an individual. The amount of the composition which is sufficient to be effective for enhancing serum DHEA levels will vary with the individual being treated and is ultimately at the discretion of the medical practitioner. The factors to be considered include the exact nature of the formulation, the individual's body weight, age and general condition, and the particular formulation to be administered. The total daily dose may be ingested in a single dose or in multiple doses, preferably in two doses per day.

EXAMPLES

The DHEA serum levels of over 2000 individuals were initially determined. Of these individuals, 1800 were patients with a wide variety of illnesses, and approximately 200 were students or staff with no known illnesses; over 90% of these individuals have DHEA levels well below the laboratory mean. Of patients with illnesses, not one has had a DHEA level above the mean. Indeed, approximately 25% of chronically ill patients have DHEA levels well below the limits of "Normal" by laboratory standards. Of the "healthy controls," none had DHEA levels which fell below the lower limits of normal, and 10% had levels above the mean.

All DHEA serum measurements of samples of blood taken from subjects were performed by Nichols Corning Labs of Capistrano, California. All DHEA serum measurements herein are accurate to within +/−5%.

From these measurements, it appears that the "Normal" value for DHEA serum levels for men is in the range of 180–1250 ng/dl, and for women the "Normal" value for DHEA serum level ranges between 130–980 ng/dl. The mean value for men is approximately 715 ng/dl, and for women is approximately 555 ng/dl.

It was noted that exceptionally healthy persons had serum DHEA levels at the upper end of the range determined, independent of the age of the individual tested. One 59 year old female individual in the sample had a DHEA level of 658 ng/dl of DHEA. Overall, the healthiest individuals in this sample had DHEA levels 20% or more above the mean. In fact, all patients (over 1800) treated at the Shealy Institute (1328 E. Evergreen, Springfield, Mo.)) over a period of six years who evidenced any type of illness had DHEA serum levels well below the appropriate mean DHEA serum levels.

DHEA levels are relatively stable; there is not more than 15% variation in serum DHEA levels either seasonally or diurnally. Additional evidence obtained from over 150 patients of the Shealy Institute and 20 healthy volunteers indicates that DHEA levels do not change significantly (less than 15%) over many months, unless the individuals are treated, either as previously described (U.S. patent application Ser. No. 08/390,965), now U.S. Pat. No. 5,609,617 or with the effective compositions by the methods of using them as described in this application.

In evaluating the effect of various compositions on serum DHEA levels, several were found to be ineffective in raising serum DHEA levels. These compositions include:

Example I

| Composition: | |
|---|---|
| Wild Yam Root | about 3,200 mg/day |
| Treatment Duration: | 3 months |
| Subjects: | 6 females, 4 males |
| | total 10 |
| | ages 32 to 66 |

Results:
No effect on serum DHEA levels

Example II

| Composition: | |
|---|---|
| Adrenoplex | about 232 mg, 3 × /day |
| Treatment Duration: | 3 months |
| Subjects: | 4 females, 5 males |
| | 9 total |
| | ages 30 to 65 |

Results:
No effect on serum DHEA levels

Example III

| Composition: | |
|---|---|
| Blue Green Alae | 2,000 mg/day |
| Treatment Duration: | 3 months |
| Subjects: | 5 females, 4 males |
| | 9 total |
| | ages 30 to 74 |

Results:
No effect on serum DHEA levels

Example IV

| Composition: | |
|---|---|
| Methyl Sulfonyl Methane | 500 mg/day |
| Treatment Duration: | 3 weeks |
| Subjects: | 4 females, 4 males |
| | 8 total |
| | ages 26 to 63 |

Results:
No effect on serum DHEA levels

Example V

| Composition: | |
|---|---|
| Vitamin C | 2,000 mg/day |
| Treatment Duration: | 1 month |
| Subjects: | 10 females, 2 males |
| | 12 total |
| | ages 28 to 60 |

Results:
No effect on serum DHEA levels

However, the following two compositions were found to be effective in increasing serum DHEA levels:

Example VI

| Composition: | |
|---|---|
| Methyl Sulfonyl Methane (MSM) | about 1,500 mg/day |
| Vitamin C | about 2,000 mg/day |
| Treatment Duration: | one month |
| Subjects: | 56 females, 7 males |
| | 63 total |
| | 24–68 |

Results:
8 individuals (5 females and 3 males) evidenced increased serum DHEA levels of 30% to 120% over baseline levels.

Example VII

| Composition: | |
|---|---|
| Methyl Sulfonyl Methane (MSM) | about 1,500 mg/day |
| Vitamin C | about 2,000 mg/day |
| Beta-1,3-Glucan | about 2.3 mg/day |
| Treatment Duration: | 4 weeks |
| Subjects: | 18 females, 2 males |
| | 20 total |

Results:
14 individuals (12 females and 2 males) evidenced increased serum DHEA levels of 50% to 150% over baseline levels.

An increase in serum DHEA levels was observed as early as after one week of treatment with the regime described in Example VII. In three individuals, increased DHEA levels were observed after four months of continuing treatment with the regime described in Example VII.

As discussed supra, Loria et al. demonstrated a strong correlation between enhanced immune response and serum DHEA levels. Loria et al. stated that increased serum DHEA levels could provide a very high amount of protection against many pathogenic viral, bacterial, and fungal infections, including opportunistic infections. It was also postulated that raising levels of DHEA in patient's serum is of value in the treatment of immunocompromised individuals suffering from AIDS or of those infected with the HIV virus showing the AIDS related complex (ARC).

Eich et. al, supra, demonstrated that elevated levels of DHEA and DHEA-S in patient's serum resulted in lower rates of platelet aggregation. It is well known that reducing the rate of platelet aggregation has significant health benefits, including, but not limited to, reduction in the incidence of mortality from vascular events such as a stroke, and also reduces the occurrence of restenosis following vascular interventions. Therefore, by raising serum DHEA levels in individuals via treatment utilizing the methods of the current invention, health benefits are expected.

It is understood that the invention is not confined to the particular embodiments set forth herein as illustrated, but embraces all such modifications thereof as come within the scope of the following claims.

What is claimed is:

1. A composition for use in enhancing serum dehydroepiandrosterone (DHEA) levels in humans comprising:
    a) an effective amount of methyl sulfonyl methane,
    b) an effective amount of vitamin c, and
    c) an effective amount of beta-1,3-glucan, which together exhibit activity increasing serum DHEA levels.

2. The composition of claim 1 wherein the composition is in suitable formulation for administration to humans in oral form.

3. The composition of claim 2 wherein the formulation suitable for administration to humans in oral form is selected from the group consisting of dried powder mix, liquid, tablet, and capsule.

4. The composition of claim 1 wherein methyl sulfonyl methane is in the range of about 150 to 1500 mg.

5. The composition of claim 4 wherein methyl sulfonyl methane is about 1500 mg.

6. The composition of claim 1 wherein vitamin C is in the range of about 200 to 2000 mg.

7. The composition of claim 6 wherein vitamin C is about 2000 mg.

8. The composition of claim 1 wherein beta-1,3-glucan is in the range of about 0.4 to 6 mg.

9. The composition of claim 1 wherein beta-1,3-glucan is in the range of about 2 to 3 mg.

10. The composition of claim 1 wherein methyl sulfonyl methane is in the range of about 150 to 1500 mg, vitamin C is in the range of about 200 to 2000 mg, and beta-1,3-glucan is in the range of about 0.4 to 6 mg.

11. The composition of claim 10 wherein methyl sulfonyl methane is about 1500 mg, vitamin C is about 2000 mg, and beta-1,3-glucan is in the range of about 2 to 3mg.

* * * * *